US00PP26832P2

(12) United States Plant Patent
van Noort

(10) Patent No.: US PP26,832 P2
(45) Date of Patent: Jun. 14, 2016

(54) ***GERANIUM* PLANT NAMED 'NOORTSALMON'**

(50) Latin Name: *Geranium cinereum*
Varietal Denomination: Noortsalmon

(71) Applicant: Marco van Noort, Warmond (NL)

(72) Inventor: Marco van Noort, Warmond (NL)

(73) Assignee: Marco van Noort Breeding BV, Warmond (NL)

( * ) Notice: Subject to any disclaimer, the term of this patent is extended or adjusted under 35 U.S.C. 154(b) by 16 days.

(21) Appl. No.: 14/544,141

(22) Filed: Dec. 2, 2014

(51) Int. Cl.
*A01H 5/02* (2006.01)

(52) U.S. Cl.
USPC ..... Plt./324

(58) Field of Classification Search
USPC ..... Plt./324
CPC ..... A01H 5/02; A01H 5/0277
See application file for complete search history.

*Primary Examiner* — Kent L Bell
(74) *Attorney, Agent, or Firm* — Penny J. Aguirre

(57) ABSTRACT

A new cultivar of *Geranium cinereum*, 'Noortsalmon', that is characterized by its flowers that are salmon pink in color and consistent in color throughout the plant, its floriferous bloom habit, and its resistance to soil fungi diseases common to other *Geranium* cultivars.

2 Drawing Sheets

Botanical classification: *Geranium cinereum.*
Cultivar designation: 'Noortsalmon'.

BACKGROUND OF THE INVENTION

The present invention relates to a new and distinct cultivar of *Geranium* plant, botanically known as *Geranium cinereum* 'Noortsalmon' and will be referred to hereafter by its cultivar name, 'Noortsalmon'.

'Noortsalmon' was derived from a breeding program conducted by the Inventor in Warmond, The Netherlands. The objectives of the breeding program were to develop new cultivars of *Geranium cinereum* in a range of flower colors that commence bloom early in the season and exhibit disease resistance, compact plant habits and rain resistance. 'Noortsalmon' arose from a cross made from in summer of 2010 between an unnamed and unpatented plant of *Geranium cinereum* from the Inventor's breeding program as the female parent and *Geranium cinereum* 'Splendens' (not patented), as the male parent. The Inventor selected 'Noortsalmon' as a single unique plant amongst the seedlings that resulted from the above cross in May of 2012.

Asexual propagation of the new cultivar was first accomplished by in vitro propagation by the Inventor in Otrebusy, Poland in April of 2014. Asexual propagation by in vitro propagation and root cuttings has determined that the characteristics of the new cultivar are stable and are reproduced true to type in successive generations.

SUMMARY OF THE INVENTION

The following traits have been repeatedly observed and represent the characteristics of 'Noortsalmon'. These attributes in combination distinguish 'Noortsalmon' as a new and distinct cultivar of *Geranium.*

1. 'Noortsalmon' exhibits flowers that are salmon pink in color.
2. 'Noortsalmon' exhibit a floriferous bloom habit.
3. 'Noortsalmon' exhibits greater resistance to soil fungi relative to other *Geranium cinereum* cultivars.

4. 'Noortsalmon' exhibits flowers that are consistent in color throughout the plant.

The female parent of 'Noortsalmon' differs from 'Noortsalmon' in having flowers that are light pink in color. The male parent of 'Noortsalmon', 'Splendens' is similar to 'Noortsalmon' in overall plant shape. 'Splendens' differs from 'Noortsalmon' in having flowers that are deep pinkish purple in color. 'Noortsalmon' can also be compared to the *Geranium cinereum* cultivar, 'Signal' (not patented). 'Signal' is similar to 'Noortsalmon' in overall plant shape. 'Signal' differs from 'Noortsalmon' in having flowers that are deep reddish purple in color.

BRIEF DESCRIPTION OF THE DRAWINGS

The accompanying colored photographs illustrate the overall appearance and distinct characteristics of the new *Geranium*. The photographs were taken of a one year-old plant of 'Noortsalmon' as field grown in Warmond, The Netherlands and placed in a container for the photographs.

The photograph in FIG. 1 provides an overall view of a plant of 'Noortsalmon' in bloom.

Figure 1:
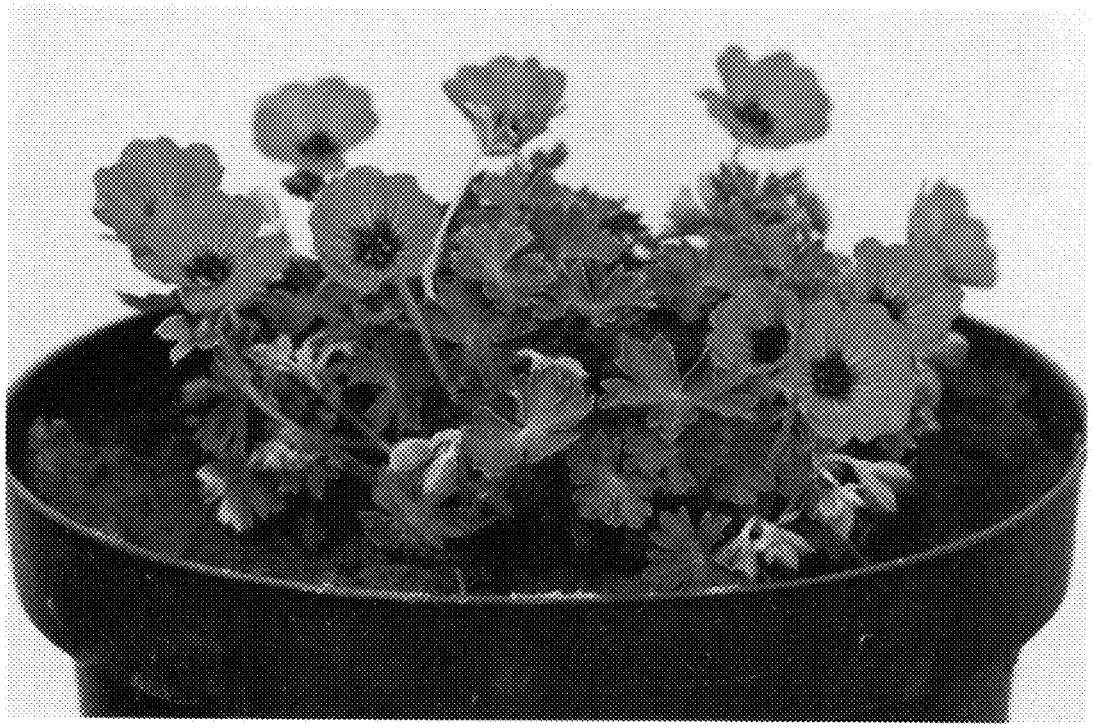
Figure 2:
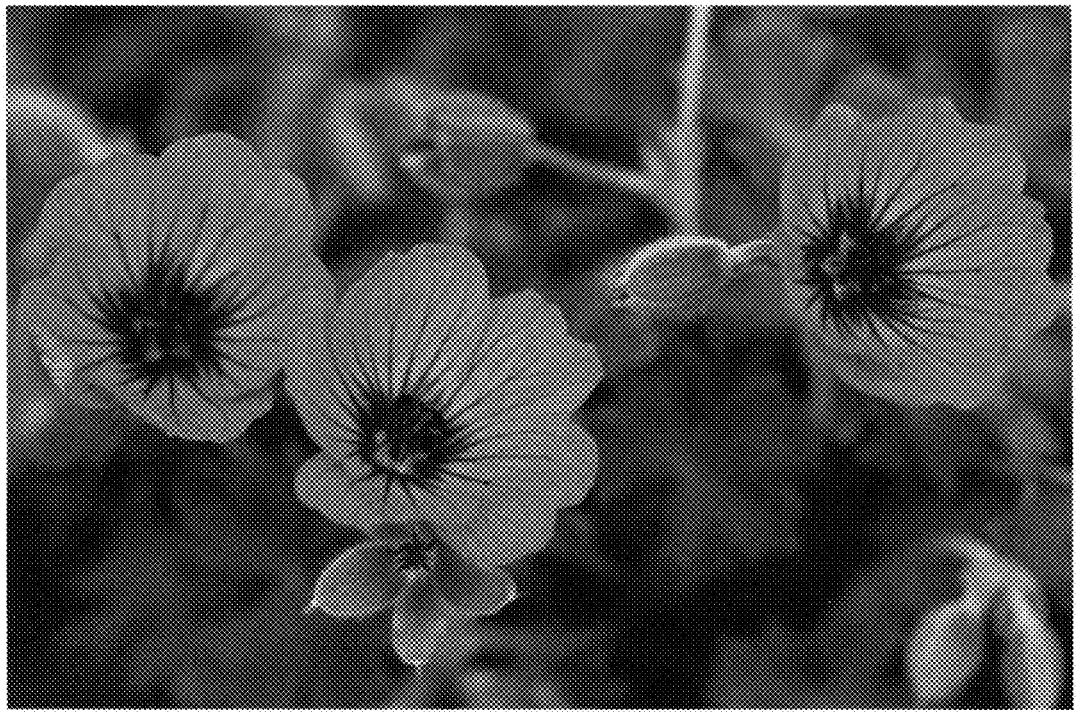

The photograph in FIG. 2 provides a close-up view of the flowers of 'Noortsalmon'.

Figure 3:
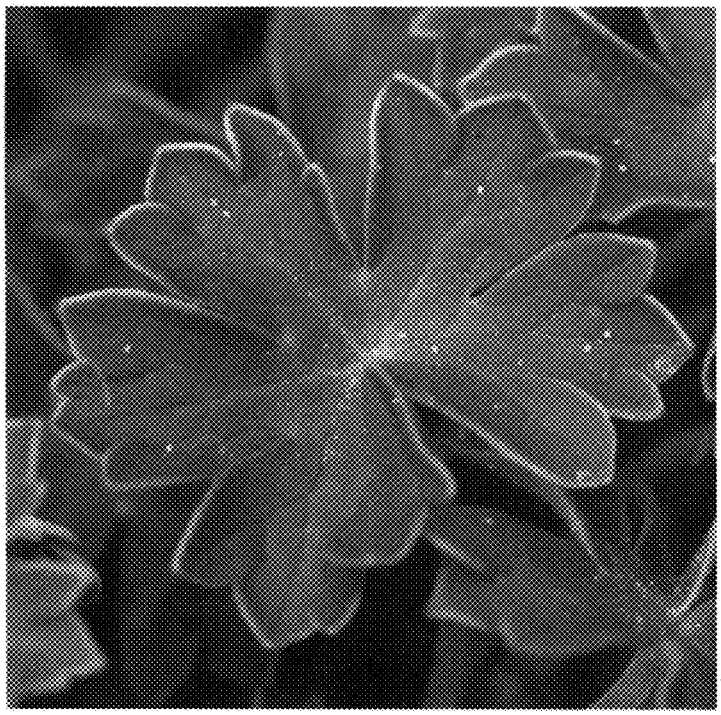

The photograph in FIG. 3 provides a close-up view of the foliage of 'Noortsalmon'.

The colors in the photographs are as close as possible with the digital photography techniques available, the color values cited in the detailed botanical description accurately describe the colors of the new *Geranium.*

DETAILED BOTANICAL DESCRIPTION OF THE PLANT

The following is a detailed description of one year-old plants of the new cultivar as field grown outdoors in Warmond, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—April to June in The Netherlands.

*Plant type.*—Herbaceous perennial.

*Plant habit.*—Low growing, spreading, and flattened with flowers held above the foliage.

*Height and spread.*—An average of 8.2 cm in height and 17.4 cm in spread as a one year-old plant in the garden.

*Cold hardiness.*—At least to U.S.D.A. Zone 5.

*Diseases.*—Observed to have some resistance to soil fungi caused by *Botrytis cinerea* and *Pythium* spp.

*Root description.*—Fibrous and fine, primarily 176A and 176B in color.

*Root development.*—An average of 20 weeks to fully develop from a rooted cutting in a 9-cm container.

*Growth rate.*—Moderate, about 7 cm per month in spring.

*Propagation.*—In vitro propagation (preferred) and root cuttings.

Stem description:

*Stem size.*—Average of 5.2 cm in length and 1.5 mm in width.

*Stem shape.*—Round.

*Stem color.*—145B.

*Stem surface.*—Slightly glossy with stems densely covered with very short soft adpressed hairs; average of 0.5 mm in length and too small to measure color.

*Stem strength.*—Moderately strong.

*Internode length.*—Average of 2.3 cm.

*Branching.*—Freely branched with an average of 20 lateral branches.

Foliage description:

*Leaf shape.*—Reniform (in outline), palmately deeply cleft to parted with an average of five lobes.

*Leaf division.*—Simple.

*Leaf base.*—Hastate.

*Leaf apex.*—Abruptly acute.

*Leaf venation.*—Palmate, color of upper side 143A, color of lower side 144B.

*Leaf margins.*—Palmately deeply cleft to parted into an average of five lobes, margins of lobes are entire with 3 dentations at apex.

*Leaf attachment.*—Petiolate.

*Leaf arrangement.*—Opposite.

*Leaf surface.*—Both sides matte and densely covered with short and soft adpressed hairs, average of 0.5 mm in length and too small to measure color.

*Leaf size.*—Average of 2 cm in length and 2.3 cm in width.

*Leaf color.*—Upper and lower surface young; 137B, upper surface mature; color N137C to N137B, lower surface mature; 138B.

*Leaf quantity.*—Average of 6 leaves per lateral branch.

*Petioles.*—Average of 8.5 cm in length and 1 mm in diameter, surfaces are 145A in color, surface puberulent.

*Stipules.*—2 leafy stipules are present at the base of the leaves, narrow deltoid in shape, narrow acuminate apex, truncate base, average of 5 mm in length and 2 mm in width, color; both surfaces 150D in color, both surfaces puberulent.

Flower description:

*Inflorescence type.*—Single, rotate flowers, arranged in pairs.

*Lastingness of flowers.*—About 7 days on the plant, sepals persistent.

*Flower size.*—Average of 8 mm in height and 2.9 cm in diameter.

*Flower fragrance.*—None.

*Flower number.*—Average of 8 flowers and buds per lateral stem, average of 160 per plant.

*Flower aspect*—Upright to slightly outward.

*Flower buds.*—Elliptic to obovate in shape, average of 8 mm in length and up to 4.5 mm in diameter, 138A in color, surface densely covered with short soft hairs 1 mm in length and NN155D in color.

*Corolla features.*—Petals are unfused and arranged in a rotate form, slightly cupped.

*Petal number.*—5.

*Petal shape.*—Obcordate.

*Petal color.*—When opening and fully open upper surface; 51A, fading towards base 54A to 54B, base 71A, veined N186C, when opening and fully open lower surface; 54B, fading towards base 54C, base N77D, veined N186C.

*Petal surface.*—Both surfaces matte and velvety.

*Petal margins.*—Entire with retuse apex.

*Petal apex.*—Retuse.

*Petal size.*—Average of 1.9 cm in length and 1.7 cm in width.

*Calyx.*—Rotate and cupped, 4 mm in length and 1.6 cm in diameter.

*Sepals.*—5, ovate in shape, average of 1 mm length and 4 mm in width, entire margin, mucronate apex, cuneate base, both surfaces matte, color young and mature upper surface; 143A, color young and mature lower surface; 137C.

*Peduncles.*—Round in shape, average of 3.1 cm in length and 1 mm in diameter, strong, held at a 35° angle to the lateral branch, color of surfaces are 145A, upper surface (sun exposed) tinged 177D, surface puberulent.

*Pedicels.*—Round in shape, average of 9 mm in length and 0.75 mm in diameter, strong, one flower straight on top of peduncle, the second flower held in an average angle of 25° to lateral branch, color of surfaces are 144A, upper surface (sun exposed) tinged 176C, surface puberulent.

Reproductive organs:

*Gynoecium.*—1 pistil, average of 5 mm in length, 5 stigmas are decurrent (reflexed) and 187A in color, style is an average of 3.5 mm in length and 146D in color, ovary is 143A in color.

*Androecium.*—10 stamens, anthers are dorsifixed, oblong in shape and held at a 90° angle on top of filament, 1.5 mm in length, and 203A in color, filaments are 5 mm in length and N186D in color, pollen is low in quantity and 10A in color.

*Fruit/seeds.*—None detected.

It is claimed:

1. A new and distinct cultivar of *Geranium* plant named 'Noortsalmon' as herein illustrated and described.

* * * * *